United States Patent [19]

Smith et al.

[11] 4,376,027
[45] Mar. 8, 1983

[54] PORTABLE ELECTROLYTIC TESTING DEVICE FOR METALS

[76] Inventors: Joseph J. Smith, 2601 Knollwood Rd., Charlotte, N.C. 28211; Thomas L. Moseley, 9352 Pinewood St., Charlotte, N.C. 28214

[21] Appl. No.: 267,545

[22] Filed: May 27, 1981

[51] Int. Cl.³ ............................................. G01N 27/46
[52] U.S. Cl. ................................................. 204/195 R
[58] Field of Search ........................... 204/1 T, 195 R

[56] References Cited

U.S. PATENT DOCUMENTS

| | | | |
|---|---|---|---|
| 2,531,747 | 11/1950 | Stearn | 204/195 R |
| 2,760,921 | 8/1956 | Pollack | 204/1 T |
| 2,930,747 | 3/1960 | Jankowski | 204/195 R |
| 3,282,804 | 11/1966 | Stearn | 204/1 T |
| 3,366,554 | 1/1968 | Lindblad | 204/1 T |
| 3,463,717 | 8/1969 | Koopman et al. | 204/195 F |
| 3,975,681 | 8/1976 | Angelini et al. | 204/1 T |
| 4,006,063 | 2/1977 | Ensanian | 204/1 T |
| 4,179,349 | 12/1979 | Park | 204/195 F |
| 4,190,501 | 2/1980 | Riggs | 204/1 T |
| 4,213,841 | 7/1980 | Jungman | 204/195 R |

*Primary Examiner*—T. Tung
*Attorney, Agent, or Firm*—Bell, Seltzer, Park & Gibson

[57] ABSTRACT

A compact, self-contained, portable electrolytic testing device has a housing which carries an electrical test circuit and a container of an electrolytic solution for use with electrodes of the test circuit for quickly and readily determining the presence of a given metal in a variety of metal alloys.

13 Claims, 6 Drawing Figures

U.S. Patent     Mar. 8, 1983     4,376,027
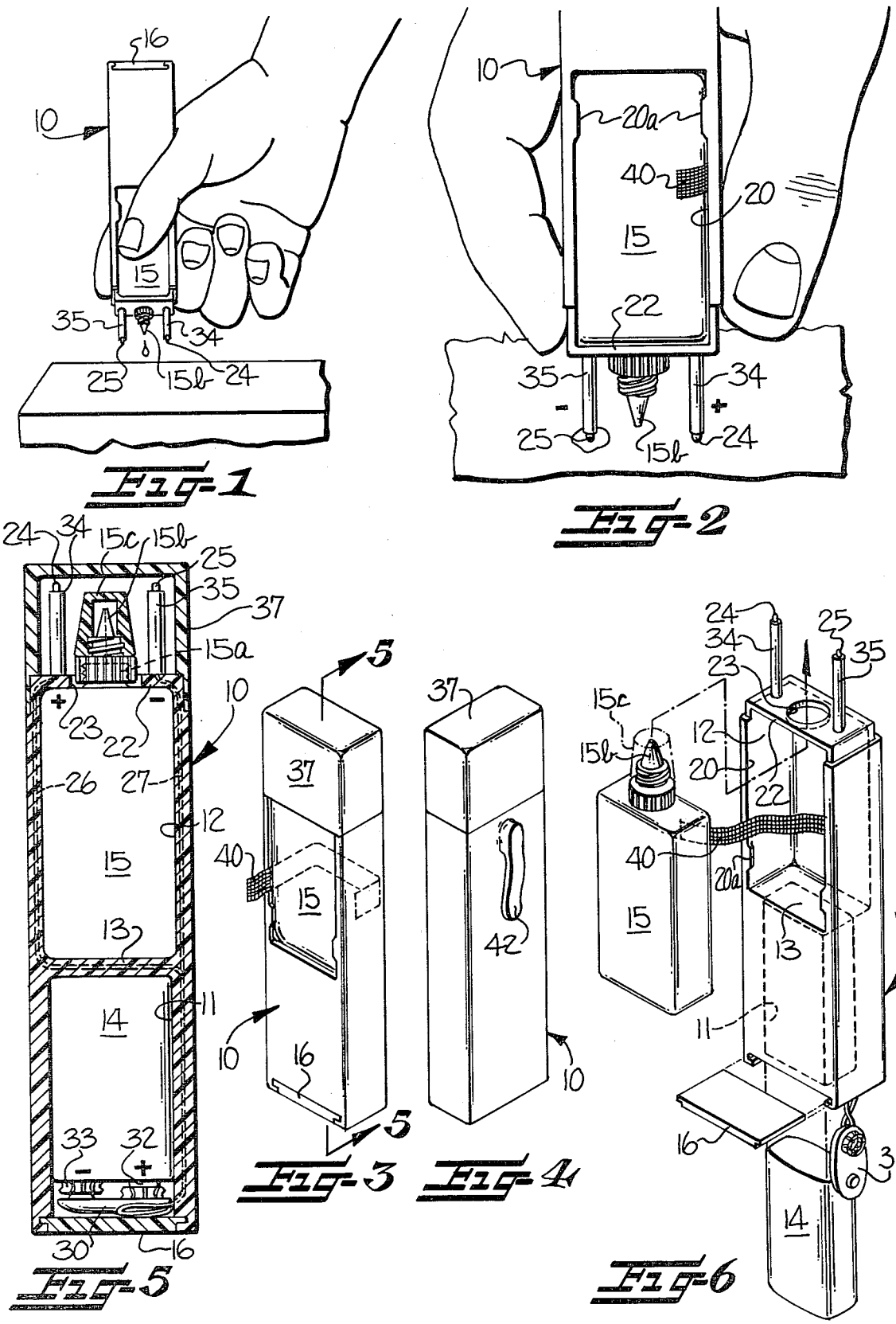

PORTABLE ELECTROLYTIC TESTING DEVICE FOR METALS

This invention relates to apparatus for testing metals, and more especially to an improved portable testing device for readily determining whether a given metal is present in a variety of metal alloys.

In the scrap metal industry, it is well known that some metal alloys are of greater value than others by virtue of the presence of given valuable metals, such as molybdenum, in such metal alloys and which given metals might not be readily detectable in the alloys. Typically, to determine the presence of a given metal in metal alloys, a small amount of an electrically responsive color-forming solution, i.e., an electrolytic solution, is deposited on a piece of metal alloy to be tested, and then a pair of positive and negative electrodes extending from a storage battery are positioned in contact with the alloy with only the negative electrode contacting the deposited electrolytic solution. A consequent change in the appearance, i.e., color, of the deposited electrolytic solution serves as a visual indication that the given metal is present in the alloy being tested.

Prior metal alloy testing devices are relatively complex, they are relatively expensive, and they are not self-contained. Also, such prior testing devices are quite bulky and heavy, and they are not readily carried, particularly when being transported over piles or stacks of pieces of metal alloy such as are found in scrap metal storage areas.

With the foregoing in mind, it is an object of this invention to provide a compact, self-contained, portable electrolytic testing device for quickly and readily determining the presence of a given metal in a variety of metal alloys, and which testing device is of such size and lightweight construction that it can be readily carried in the hand of a user.

BRIEF DESCRIPTION OF THE DRAWINGS

An object and advantages of the invention having been stated, others will appear as the description proceeds when taken in connection with the accompanying drawings, in which FIGS. 1 and 2 are perspective views illustrating successive stages in the use of a preferred embodiment of the electrolytic testing device of the present invention;

FIG. 3 is a perspective view looking down at the top, front and one side of the testing device, with a protective cover positioned over the electrodes thereof;

FIG. 4 is a perspective view looking down at the top and rear of the testing device and also looking at the same side of the device as is shown in FIG. 3;

FIG. 5 is an enlarged vertical sectional view taken substantially along line 5—5 in FIG. 3; and FIG. 6 is a partially exploded perspective view of the testing device, and omitting the protective cover from the housing.

While this invention will be described hereinafter with particular reference to the accompanying drawings in which an illustrative embodiment of the present invention is set forth, it is to be understood at the outset of the description which follows that it is contemplated that persons skilled in the applicable arts may modify the specific details to be described while continuing to use this invention. Accordingly, the description is to be understood as a broad teaching of this invention, directed to persons skilled in the applicable arts.

Referring more specifically to the drawings, a preferred embodiment of the electrolytic testing device of the present invention is there shown and comprises a housing broadly designated at 10. Housing 10 is made of a lightweight material, preferably a plastic material, and is preferably of elongate substantially rectangular form, as illustrated.

Housing 10 is provided with a pair of elongate, walled compartments 11, 12, which are preferably longitudinally aligned with each other and are separated from each other by a transverse wall or partition 13 in housing 10. The compartments 11, 12 are of such size and shape as to readily receive and firmly hold therein a relatively small dry-celled storage battery 14 and a pliable-walled container means 15, respectively. The container means 15, hereinafter referred to as a container, is in the form of a so-called "squeeze bottle" containing therein an electrically responsive color-forming solution, generally known as an electrolytic solution. The lower end of compartment 11 is provided with an access opening normally closed by a suitable access cover or door 16 slideably mounted, as by tongue and groove connections, between the lower portions of opposing side walls of the housing 10.

To facilitate manually squeezing and deforming the container 15 for dispensing electrolytic solution therefrom (see FIG. 1), the front wall of housing 10 is cut away to provide an access opening 20 at one side of the compartment 12 therein and through which one side wall of the container 15 is exposed so as to be engaged and depressed or squeezed by a finger or fingers of the user of the testing device. The upper end of the container compartment 12 is provided with an end wall 22 having an opening 23 therethrough through which a projecting neck portion 15a of container 15 loosely extends when the container is properly positioned in the compartment 12. The neck portion 15a has a conical discharge spout or nozzle 15b threaded thereonto through which small amounts of the electrolytic solution may be dispensed from the container 15 when desired. When the testing device is not being used, the spout 15b may be closed by a suitable closure cap 15c threaded onto the spout 15b.

Conveniently, the discharge spout 15b of container 15 is positioned between a pair of positive and negative electrodes 24, 25 electrically connected, via conductors 26, 27 and an electrical terminal connector 30, to the respective positive and negative terminals 32, 33 extending from the lower end of storage battery 14. The conductors 26, 27 may be embedded in the walls of the housing 10 as shown in FIG. 5. Desirably, the storage battery 14 is of the standard 9-volt type in general use in flashlights, calculators, pocket radios, and the like, and which are about one inch wide, five-eighths inch thick, and one-and-seven-eighths inch long (25.4×15.9×47.5 mm). It should be noted that the length of the battery compartment 11 is such as to accommodate both the battery 14 and the terminal connector 30 therein when the cover 16 occupies the fully closed position in which it is shown in FIGS. 3 and 5.

From the foregoing description, it can be appreciated that the storage battery 14, the electrodes 24, 25, the conductors 26, 27, and the terminal connector 30 collectively define an electrical test circuit carried by housing 10.

As shown in FIGS. 1, 2 and 5, it is preferred that the electrodes 24, 25 are in the form of relatively rigid posts or wires extending outwardly from the housing end wall 22 in a substantially common direction and in generally parallel relationship for a distance somewhat greater than that of the discharge end of the spout 15b of container 15. To aid a person in the proper use of the electrolytic testing device for proper test results, the electrodes 24, 25 should be readily distinguishable from each other so that the negative electrode may be placed in the electrolytic solution and the positive electrode may be placed in contact with the metal alloy to be tested. This distinguishing of the electrodes may be effected in a variety of different ways, as by applying identifying indicia or a color code to one or both electrodes. Preferably, one or more color-coded sleeves are utilized, such as identifying sleeves 34, 35. These sleeves may be formed of a plastic material and may be secured on the electrodes 24, 25 by being heat-shrunk thereon. By way of example, the sleeve 34 on the positive electrode 24 may be red in color and the sleeve 35 on the negative electrode 25 may be black to facilitate quick visual identification of the electrodes 24, 25. When the electrolytic testing device is not in use, a protective closure cap 37, preferably made from a plastic material, may be positioned over the electrodes 24, 25 and in engagement with the upper end portion of the housing 10.

As indicated earlier herein, it is preferred that the container 15 fits snugly in the compartment 12. To aid in retaining the container 15 in the compartment 12, it will be observed in FIGS. 1, 2, 3 and 6 that the front wall of housing 10 is provided with a pair of relatively small projecting tab portions 20a which project into the opening 20 at opposite sides thereof and are positioned adjacent the lower portion or wall of the compartment 12 as defined by the partition 13 heretofore described. Thus, when the container 15 is placed in the compartment 12, it is inserted therein in such a manner that the spout 15b thereof is first thrust upwardly through the opening 23, and then the main body of the container 15 is manually forced inwardly past the tabs 20a as the container 15 is firmly seated in the compartment 15 and held therein by the tabs 20a.

Upon the supply of electrolytic solution in the container 15 being exhausted, the container 15 may be refilled by removing the spout 15b from the container and pouring a fresh supply of the electrolytic solution into the container 15. Alternatively, the container 15 may be removed from the compartment 12 and replaced with a full container. Accordingly, it will be observed in FIGS. 3 and 6 that one end of a pliable strap member 40 is adhesively or otherwise suitably secured to one side wall portion of the compartment 12 and extends partially around the container 15, and between the container and the rear wall of the housing 10, with a relatively short end portion of the strap member 40 projecting from the compartment 12 and through the opening 20 when the container 15 is properly installed in the compartment 12. Thus, when the container 15 is to be removed from the compartment 12, a person need only grasp the free end of the strap member 40 and exert an outward force thereon away from the housing 10 while restraining the housing from movement with the strap member 40 to thereby force the container 15 out of the compartment 12 and past the retaining tabs 20a at opposite sides of the opening 20.

As shown in FIG. 4, to facilitate carrying the testing device of the present invention from place to place, a metal or plastic yieldable clip member 42 may be adhesively or otherwise attached to the upper central portion of the outside of the rear wall of housing 10 to serve as a pocket clip for the device. In this regard, it can be readily appreciated that the size and construction of the testing device are such that it may be readily carried about in a person's shirt pocket of usual size.

The electrolytic solution in container 15 is of a type which will change color when an electrical current flows therethrough via a particular type of metal so that the presence of a given metal in an alloy being tested can be determined by a change in the color of the electrolytic solution. Various types of electrolytic solutions are known which can serve the desired purpose.

Very good results have been obtained in the testing of a group of metals utilizing an electrolytic testing device in accordance with the present invention by using a versatile electrolytic solution which is normally clear, but which turns a variety of colors for indicating the presence of a variety of different metals. This versatile solution has been utilized for identifying molybdenum, aluminum or copper—if the solution turns a pink burgundy color, the presence of molybdenum in the tested metal alloy is indicated; if the solution turns a milky white, the presence of copper is indicated; and if the solution turns a grayish black, the presence of aluminum is indicated. This versatile solution is formed of 2.5 parts of a 5% (by volume) potassium thiocyanate solution mixed with 1 part of a solution made by dissolving 25 grams of stannous chloride in 20 milliliters of concentrated (38%) hydrochloric acid which is diluted to 75 milliliters with distilled water.

In testing a metal alloy utilizing the electrolytic testing device of the present invention, for quickly determining the presence of a given metal in the metal alloy, the user simply holds the self-contained portable electrolytic testing device in one hand substantially as shown in FIG. 1 while squeezing and applying sufficient squeezing force to the container 15 to discharge a small amount or drop of the electrolytic solution through the spout 15b onto the piece of metal alloy to be tested. Thereafter, as shown in FIG. 2, the user simply positions the negative electrode 25 in contact with the previously deposited small amount of electrolytic solution on the piece of metal to be tested while positioning the positive electrode 24 against the piece of metal alloy to be tested but out of contact with the previously deposited small amount of electrolytic solution. Thereupon, current from the battery 14 flows through the electrodes and the piece of metal alloy being tested, and thus flows through the deposited small amount of electrolytic solution to effect a visual change in color of the electrolytic solution upon the detection of the presence of a given metal in the metal alloy.

It is thus seen that the present invention provides a self-contained portable electrolytic testing device which can be used for quickly determining the presence of a given metal in a variety of metal alloys and which is of such size and lightweight construction that it can be readily carried in the hand of a user, and wherein the electrodes and the electrolytic solution are carried in close proximity in a compact manner facilitating quick and easy testing of many pieces of metal alloy with very little effort on the part of the person using the testing device.

In the drawings and specification, there has been set forth a preferred embodiment of the invention, and although specific terms are employed, they are used in a generic and descriptive sense only and not for purposes of limitation.

That which is claimed is:

1. A self-contained portable electrolytic testing device adapted to be used for quickly determining the presence of a given metal in a variety of metal alloys and characterized in that the device is of such size and lightweight construction that it can be readily carried in the hand of a user, said testing device comprising a housing adapted to be readily grapsed and carried in a person's hand, an electrical test circuit carried by said housing and including a storage battery and positive and negative electrodes electrically connected to said battery and extending outwardly from said housing, an electrolytic solution for use with said electrodes, said electrolytic solution being visually changeable in color upon detection of the presence of a given metal, and container means for containing and dispensing said electrolytic solution therefrom in small amounts and being carried by the housing to thus provide the electrolytic solution readily accessible for use with the electrical test circuit for quickly determining the presence of a given metal in a variety of metal alloys.

2. A testing device according to claim 1 wherein said container means comprises a pliable-walled container adapted to be readily manually squeezed and thus deformed for dispensing said electrolytic solution therefrom.

3. A testing device according to claim 1 wherein said electrodes extend outwardly in a substantially common direction from said housing, and wherein said container means has a dispensing spout extending outwardly therefrom and outwardly from said housing and adjacent said electrodes.

4. A testing device according to claim 1 wherein means is provided in association with said electrodes for visually distinguishing the polarities of said electrodes from each other.

5. A testing device according to claim 1 wherein said electrodes are substantially rigid and extend outwardly in a substantially common direction from said housing, wherein each electrode includes an identifying sleeve thereon, and wherein said sleeve on one of said electrodes is of a visually distinct appearance relative to the sleeve on the other of said electrodes.

6. A testing device according to claim 1 wherein said housing is elongate and has substantially longitudinally aligned battery and container compartments therein, and wherein said storage battery is positioned in said battery compartment and said container means is positioned in said container compartment.

7. A testing device according to claim 6 wherein said container means comprises a manually squeezably deformable, pliable-walled container, wherein said container fits relatively snugly in said container compartment, and wherein said container compartment is open at one side thereof to facilitate manually applying a squeezing force to said container to discharge solution from said container.

8. A testing device according to claim 7 including a pliable strap member secured to said housing and extending across said container compartment and arranged to extend between said container and that side of said container compartment opposite from said open side of said container compartment with an end portion of said strap member extending outwardly through said open side of said container compartment so that said strap member can be grasped and pulled outwardly through said open side of said container compartment and relative to said housing for aiding in removing said container from its respective compartment.

9. A testing device according to claim 6 wherein said housing is provided with an access opening leading into said battery compartment, and door means normally closing said access opening and adapted to be opened for access to the storage battery in said battery compartment.

10. A testing device according to claim 6 wherein said electrodes extend outwardly from one end of said housing adjacent said container compartment, and a protective cap removably mounted on said end of said housing and overlying said electrodes.

11. A self-contained portable electrolytic testing device adapted to be used for quickly determining the presence of a given metal in a variety of metal alloys and characterized in that the device is of such size and lightweight construction that it can be readily carried in the hand of a user, said testing device comprising a housing adapted to be readily grasped and carried in a person's hand, an electrical test circuit carried by said housing and including a storage battery and positive and negative electrodes electrically connected to said battery and extending outwardly in a substantially common direction from said housing, an electrolytic solution for use with said electrodes, said electrolytic solution being visually changeable in color upon detection of the presence of a given metal, and container means carried by said housing and positioned inwardly from said electrodes for containing a supply of said electrolytic solution therein, said container means having a dispensing spout projecting outwardly therefrom and from said housing and between said electrodes to thus provide the electrolytic solution readily accessible for use with said electrodes for quickly determining the presence of a given metal in a variety of metal alloys.

12. A testing device according to claim 11 wherein said electrodes extend outwardly from said housing to a greater extent than said spout of said container means, and said container means comprises a pliable-walled container adapted to be readily squeezed manually by the user for dispensing electrolytic solution through said spout.

13. A testing device according to claim 11 wherein said housing is provided with a battery compartment for containing said storage battery therein and a container compartment for containing said container means therein, wherein said container means comprises a pliable-walled container adapted to be manually squeezed for dispensing solution therefrom through said spout, and wherein said container compartment is open along one side thereof to facilitate manually squeezing said container.

* * * * *